US00PP28941P2

(12) United States Plant Patent
Schroll

(10) Patent No.: US PP28,941 P2
(45) Date of Patent: Feb. 6, 2018

(54) ***HYDRANGEA* PLANT NAMED 'SCHROLL124-09-01'**

(50) Latin Name: *Hydrangea macrophylla*
Varietal Denomination: SCHROLL124-09-01

(71) Applicant: Soren Schroll, Odense SV (DK)

(72) Inventor: Soren Schroll, Odense SV (DK)

(73) Assignee: Scholl Management ApS, Odense SV (DK)

( * ) Notice: Subject to any disclaimer, the term of this patent is extended or adjusted under 35 U.S.C. 154(b) by 0 days.

(21) Appl. No.: 15/330,432

(22) Filed: Sep. 20, 2016

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'SCHROLL124-09-01', characterized by its compact, upright and mounded plant habit; moderately vigorous growth habit; freely branching habit and strong stems; large mophead-type inflorescences with pink-colored sterile flowers that are initially green in color during early development; and long flowering period.

2 Drawing Sheets

Botanical designation: *Hydrangea macrophylla.*
Cultivar denomination: 'SCHROLL124-09-01'.

BACKGROUND OF THE INVENTION

The present invention relates to a new and distinct cultivar of *Hydrangea* plant, botanically known as *Hydrangea macrophylla* and hereinafter referred to by the name 'SCHROLL124-09-01'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2009 of a proprietary selection of *Hydrangea macrophylla* identified as code number 04-00, not patented, as the female, or seed, parent with a proprietary selection of *Hydrangea macrophylla* identified as code number 11-00, not patented, as the male, or pollen, parent. The new *Hydrangea* plant was discovered and selected by the Inventor in February, 2011 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL124-09-01'. These characteristics in combination distinguish 'SCHROLL124-09-01' as a new and distinct *Hydrangea* plant:

1. Compact, upright and mounded plant habit.
2. Moderately vigorous growth habit.
3. Freely branching habit and strong stems.
4. Large mophead-type inflorescences with pink-colored sterile flowers that are initially green in color during early development.
5. Long flowering period.

Plants of the new *Hydrangea* differ primarily from plants of the female parent selection in the following characteristics:

1. Plants of the new *Hydrangea* have stronger stems than plants of the female parent selection.
2. Plants of the new *Hydrangea* have larger inflorescences than plants of the female parent selection.
3. Sterile flowers of plants of the new *Hydrangea* have thicker and more durable sepals than sterile flowers of plants of the female parent selection.
4. Plants of the new *Hydrangea* have longer postproduction longevity (shelf-life) than plants of the female parent selection.

Plants of the new *Hydrangea* differ primarily from plants of the male parent selection in the following characteristics:

1. Plants of the new *Hydrangea* have stronger stems than plants of the male parent selection.
2. Plants of the new *Hydrangea* have larger inflorescences than plants of the male parent selection.
3. Plants of the new *Hydrangea* have mophead-type inflorescences whereas plants of the male parent selection have lacecap-type inflorescences.
4. Plants of the new *Hydrangea* and the male parent selection differ in sterile flower color as plants of the male parent selection have sterile flowers that are dark pink in color.

5. Plants of the new *Hydrangea* have longer postproduction longevity (shelf-life) than plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are more compact than and not as vigorous as plants of 'H213901'.
2. Plants of the new *Hydrangea* flower earlier than plants of 'H213901'.
3. Inflorescences of plants of the new *Hydrangea* have more sterile flowers than inflorescences of plants of 'H213901'.
4. Sterile flowers of plants of the new *Hydrangea* are flatter than and not as folded and curly as sterile flowers of plants of 'H213901'.
5. Plants of the new *Hydrangea* and 'H213901' differ in sterile flower color as plants of 'H213901' have sterile flowers that are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the *Hydrangea* are more compact than and not as vigorous as plants of 'H213906'.
2. Plants of the new *Hydrangea* and 'H213906' differ in sterile flower color as plants of 'H213906' have sterile flowers that are dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SCHROLL124-09-01' grown in a container.

The photograph on the second sheet is a close-up view of a typical developing inflorescence of 'SCHROLL124-09-01' (top of sheet) and a developed inflorescence of 'SCHROLL124-09-01' (bottom of sheet).

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched one time and were one year old when the photographs and description were taken. During the production of the plants, day temperatures ranged from 15° C. to 25° C., night temperatures ranged from 10° C. to 20° C. and light levels ranged from 40 to 50 klux. Plants used for the description and photographs were not treated with aluminum sulfate to "blue" the inflorescences. In the following description, color references are made to The Royal Horticultural Society Colour Chart, 2007 Edition, except where general terms of ordinary dictionary significance are used.

Botanical description: *Hydrangea macrophylla* 'SCHROLL124-09-01'.

Parentage:

*Female, or seed, parent*.—Proprietary selection of *Hydrangea macrophylla* identified as code number 04-00, not patented.

*Male, or pollen, parent*.—Proprietary selection of *Hydrangea macrophylla* identified as code number 11-00, not patented.

Propagation:

*Type cutting*.—By softwood cuttings.

*Time to initiate roots, summer*.—About ten days at temperatures about 19° C. to 22° C.

*Time to initiate roots, winter*.—About two weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Low branching; sparse.

Plant description:

*Plant and growth habit*.—Perennial subshrub; compact, upright and mounded plant habit; broadly inverted triangle; freely branching habit with about six to eight lateral branches developing per plant; strong lateral branches; moderately vigorous growth habit.

*Plant height*.—About 32 cm to 35 cm.

*Plant diameter or area of spread*.—About 37 cm to 42 cm.

*Lateral branches*.—Length: About 15 cm to 20 cm. Diameter: About 5 mm to 7 mm. Internode length: About 3 cm to 4 cm. Strength: Strong. Texture: Smooth, glabrous; becoming woody with development. Color, developing: Close to 142A and 140B. Color, developed: Close to 199B. Color, lenticels: Close to N199B.

Leaf description:

*Arrangement*.—Opposite, simple.

*Length*.—About 9 cm to 9.8 cm.

*Width*.—About 6 cm to 7.5 cm.

*Shape*.—Ovate.

*Apex*.—Acute or sub-acuminate.

*Base*.—Obtuse to rounded.

*Margin*.—Serrate.

*Texture and luster, upper surface*.—Rugose, glabrous; moderately glossy to matte.

*Texture and luster, lower surface*.—Rough, glabrous; prominent venation; matte.

*Venation pattern*.—Pinnate, reticulate.

*Color*.—Developing leaves, upper surface: Close to 131A and 135A. Developing leaves, lower surface: Close to 143B. Fully expanded leaves, upper surface: Close to 131A; venation, close to 146C. Fully expanded leaves, lower surface: Close 146C; venation, close to 146C.

*Petioles*.—Length: About 2 cm. Diameter: About 8 mm to 10 mm. Strength: Strong. Texture, upper and lower surfaces: Smooth, glabrous. Color, upper surface: Close to 142B, 140C and 144C. Color, lower surface: Close to 146A.

Inflorescence & flower description:

*Flower type and habit*.—Showy single sterile and inconspicuous single fertile flowers arranged on terminal mophead-type panicles; panicles hemispherical to flattened globular in overall shape; fertile flowers face mostly upright and sterile flowers face upright to outwardly; early flowering habit, plants begin flowering about twelve weeks after planting.

*Natural flowering season*.—Continuous flowering during the summer in Northern Europe.

*Flower longevity, fertile flowers*.—Flowers last less than one month; fertile flowers not persistent.

*Flower longevity, sterile flowers*.—Long flowering period, flowers last about four months on the plant; sterile flowers persistent.

*Quantity of flowers*.—Freely flowering habit with about 100 fertile flowers and about 120 to 200 sterile flowers per panicle.

*Fragrance*.—None detected.

*Panicle height*.—About 7 cm to 11 cm.

*Panicle diameter*.—About 13 cm to 15 cm.

*Flower diameter, fertile flowers*.—About 1.5 cm to 2 cm.

*Flower depth* (*height*), *fertile flowers*.—About 3 mm to 4 mm.

*Flower diameter, sterile flowers*.—About 5 cm to 7 cm.

*Flower depth* (*height*), *sterile flowers*.—About 3 cm.

*Flower shape, fertile flowers*.—Deltoid.

*Flower shape, sterile flowers*.—Deltoid.

*Flower buds, fertile flowers*.—Length: About 3 mm. Diameter: About 2 mm to 3 mm. Shape: Flattened globular. Color: Close to 144B to 144C.

*Flower buds, sterile flowers*.—Length: About 3 mm. Diameter: About 2 mm to 3 mm. Shape: Flattened globular. Color: Close to 144C.

*Petals, fertile flowers only*.—Quantity and arrangement: Four in a single whorl; valvate. Length: About 3 mm to 3.5 mm. Width: About 2 mm. Shape: Roughly deltoid. Apex: Acute. Base: Rounded. Margin: Entire. Texture, upper surface: Smooth, glabrous. Texture, lower surface: Rough, glabrous. Color: When opening, upper surface: Close to 97A and 91B. When opening, lower surface: Close to 90D and 92B; towards the margins, close to 97B to 97C. Fully opened, upper surface: Close to 91A and 91B; towards the margins, close to 91C to 91D and 97B and 97C; color becoming closer to 76C and 84C with development. Fully opened, lower surface: Close to 76A to 76C and 91B to 91C; color becoming closer to 76C to 76D with development.

*Sepals, fertile flowers*.—Quantity and arrangement: Four in a single whorl; imbricate. Length: About 2 mm. Width: About 2 mm to 3 mm. Shape: Deltoid. Apex: Acute. Base: Rounded. Margin: Entire. Texture, upper and lower surfaces: Smooth, glabrous; velvety. Color: When opening, upper surface: Close to 75A; towards the margins, close to 75C to 75D. When opening, lower surface: Close to 75B to 75C; venation, close to 62A to 62B. Fully opened, upper surface: Close to 75A and 76A; towards the margins, close to 76B to 76C; color becoming closer to 75C with development. Fully opened, lower surface: Close to 75B; venation, close to 62A to 62B; color becoming closer to 75A and 76B to 76C with development.

*Sepals, sterile flowers*.—Quantity and arrangement: Four in a single whorl; imbricate. Length: About 2 cm. Width: About 2 cm to 2.3 cm. Shape: Deltoid. Apex: Subacute to rounded. Base: Rounded. Margin: Entire. Texture, upper surface: Smooth, glabrous. Texture, lower surface: Rugose, glabrous. Color: When opening, upper and lower surfaces: Close to 145B to 145C. Fully opened, upper surface: Close to 75A and 76A; towards the margins, close to 76B to 76C; color becoming closer to 75C with development. Fully opened, lower surface: Close to 75B; venation, close to 62A to 62B; color becoming closer to 75A and 76B to 76C with development.

*Pedicels, fertile flowers*.—Length: About 2 mm to 3.5 mm. Diameter: About 1 mm to 2 mm. Strength: Moderately strong. Aspect: Upright to slightly slanted. Texture: Smooth, glabrous. Color: Close to 62B to 62C.

*Pedicels, sterile flowers*.—Length: About 2 mm. Diameter: About 2 mm. Strength: Strong. Aspect: About 30° to 35° from vertical. Texture: Smooth, glabrous. Color: Close to 62B and 68C to 68D.

*Reproductive organs, fertile flowers only*.—Stamens: Quantity per flower: About eight. Filament length: About 1 mm to 2 mm. Filament color: Close to N88A to N88B. Anther length: Less than 1 mm. Anther shape: Two-lobed, conical. Anther color: Close to N88A to N88B. Pollen amount: Abundant. Pollen color: Close to 155D. Pistils: Pistil quantity per flower: About three. Pistil length: About 1.5 mm to 2 mm. Stigma shape: Club-shaped. Stigma color: Close to 84A and N87B to N87C. Style length: About 1 mm to 1.5 mm. Style color: Close to 84A and N88A.

*Seeds*.—Quantity: Numerous. Color: Close to 200C.

Disease & pest resistance: Plants of the new *Hydrangea* have been observed to be resistant to spider mites; plants of the new *Hydrangea* have not been observed to be resistant to pathogens and other pests common to *Hydrangea* plants.

Temperature tolerance: Plants of the new *Hydrangea* have been shown to be tolerant to temperatures ranging from −5° C. to 35° C.

It is claimed:

1. A new and distinct *Hydrangea* plant named 'SCHROLL124-09-01' as illustrated and described.

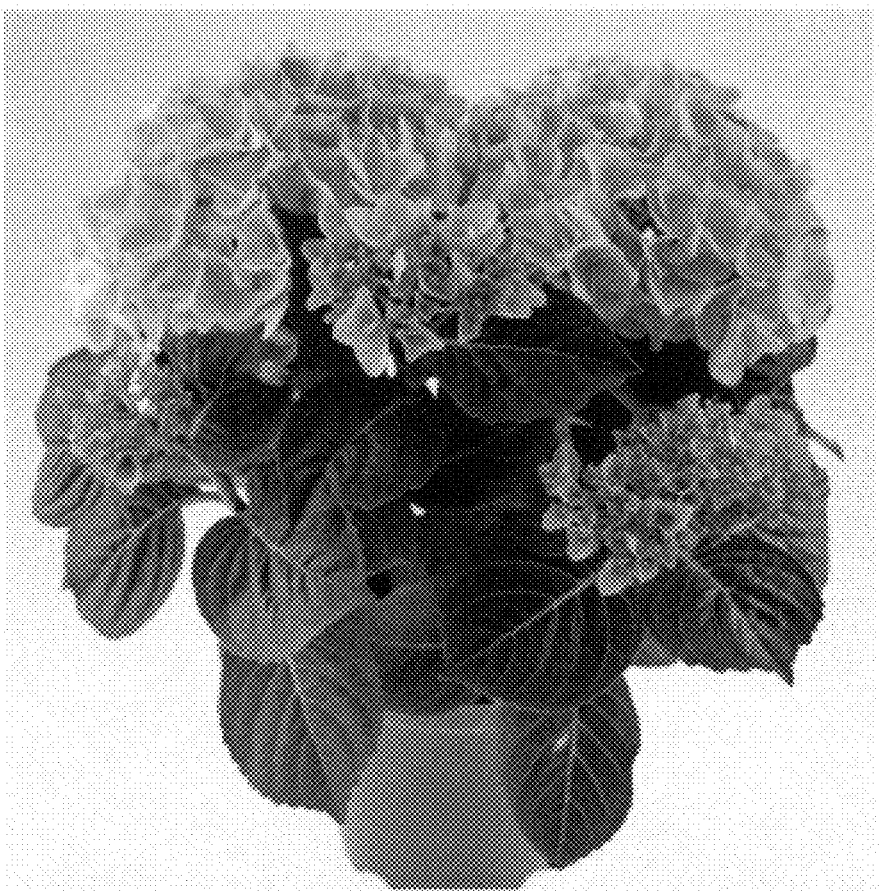

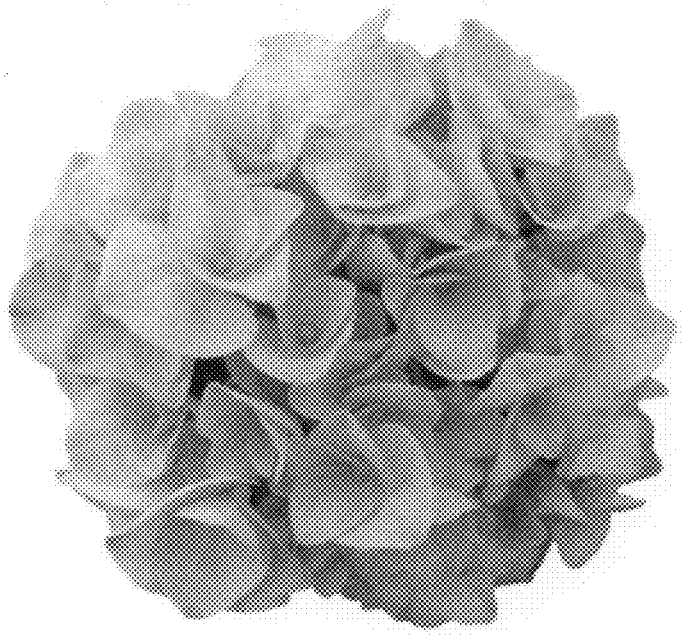
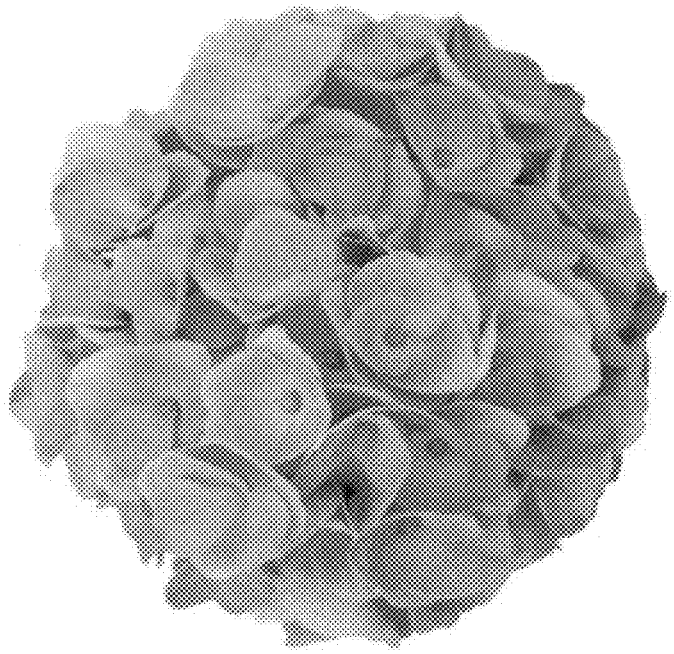

* * * * *